United States Patent [19]

Sevenét et al.

[11] 4,033,969
[45] July 5, 1977

[54] VINCAMINE DERIVATIVES

[75] Inventors: Thierry Sevenét, Gif-sur-Yvette; Claude Thal, Malakoff; Pierre Potiér, Bois d'Arcy; Henri Philippe Husson, Chevreuse, all of France

[73] Assignee: Agence Nationale de Valorisation de la Recherche (ANVAR), Neuilly-sur-Seine, France

[22] Filed: Sept. 29, 1975

[21] Appl. No.: 617,695

Related U.S. Application Data

[63] Continuation-in-part of Ser. No. 370,334, June 15, 1973, Pat. No. 3,937,709.

[30] Foreign Application Priority Data

June 19, 1972 France .................. 72.220210

[52] U.S. Cl. .................. 260/293.53; 424/267
[51] Int. Cl.² .................. C07D 459/00
[58] Field of Search .................. 260/293.53

[56] References Cited
UNITED STATES PATENTS

| | | | |
|---|---|---|---|
| 3,454,583 | 7/1969 | Kuehne | 260/294.3 |
| 3,770,724 | 11/1973 | Warnant et al. | 260/239.3 P |
| 3,830,823 | 8/1974 | Castaigne | 260/293.53 |

Primary Examiner—Natalie Trousof
Attorney, Agent, or Firm—Eric P. Schellin

[57] ABSTRACT

New compounds having the formula

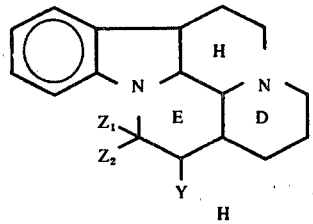

in which Y represents a hydrogen atom, in which case $Z_1$ and $Z_2$ represent simultaneously an oxygen atom, or $Z_1$ represents a methoxycarbonyl radical and $Z_2$ a hydroxy radical, or Y and $Z_2$ form together a carbon-carbon bond and $Z_1$ is a methoxycarbonyl radical, said compounds being additionally characterized by a cis-fusion of the D/E rings. Said new compounds and vincamine and certain of its derivatives are prepared from an enamine having the formula :

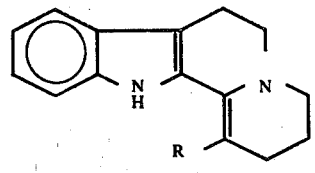

in which R is H or $C_2H_5$.

1 Claim, No Drawings

VINCAMINE DERIVATIVES

This application is a continuation-in-part of the U.S. application Ser. No. 370,334, filed June 15, 1973, now U.S. Pat. No. 3,937,709.

This invention relates to new vincamine derivatives and to a novel process for the preparation of vincamine and of vincamine derivatives.

It is known that vincamine possesses highly useful therapeutic properties and that it may be used for the treatment of cerebral vascular conditions.

The chemical synthesis of vincamine has already been effected, for example by M. E. KUEHNE (J. Am. Chem. Soc., 1964, 86, 2946) and by K. H. GIBSON and J. E. SAXTON (Chem. Comm., 1969, 1940).

Both the above mentioned methods have various drawbacks, particularly in that they lead, at different stages, to a mixture of isomers and make it possible to obtain vincamine only with low yields.

According to the process of this invention, vincamine and its derivatives are prepared from an enamine (compound described by R. N. Schut and T. J. Leipzig, J. Het. Chem., 1966, 3, 101).

The new vincamine derivatives included within the scope of the invention have the general formula:

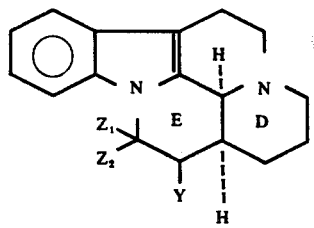

in which:
Y represents a hydrogen atom, in which case $Z_1$ and $Z_2$ represent simultaneously an oxygen atom, or $Z_1$ represents a methoxycarbonyl radical and $Z_2$ represents a hydroxy radical, or
Y and $Z_2$ form together a carbon-carbon bond and $Z_1$ is a methoxycarbonyl radical,
said compounds being additionally characterized by a cis-fusion of the D/E rings.

Said compounds are analogs of alkaloids of the deethyleburnane group.

The invention includes in particular within its scope 20-deethyl-vincamine, 20-deethyl-apovincamine and 20-deethyleburnamonine as their racemic and optically active forms.

The process for the preparation of vincamine and its derivatives which are described in the present application comprises condensing an enamine (1) with methyl α-bromomethyl-acrylate prepared according to the method disclosed by A. R. FERRIS (J. Org. Chem., 1955, 20, 780). The resulting immonium salt (2) is reduced with sodium borohydride to give compound (3). The group $>C=CH_2$ of compound (3) is oxidized in the presence of periodic acid with potassium permanganate or osmium tetraoxide according to the method disclosed by S. M. KUPCHAN (J. Org. Chem., 1962, 3103). The resulting ketone condenses immediately with the indole >NH group to give compound (4) which is vincamine where R is ethyl or 20-deethyl-vincamine when R is H. On dehydration under acidic conditions, 20-deethyl-vincamine leads to compound (5), 20-deethyl-apovincamine.

Compound (4) may be reacted with lithium aluminum hydride within tetrahydrofuran and then with hot hydrochloric acid, to give compound (7.

Diagram I below illustrates the process for the preparation of said compounds.

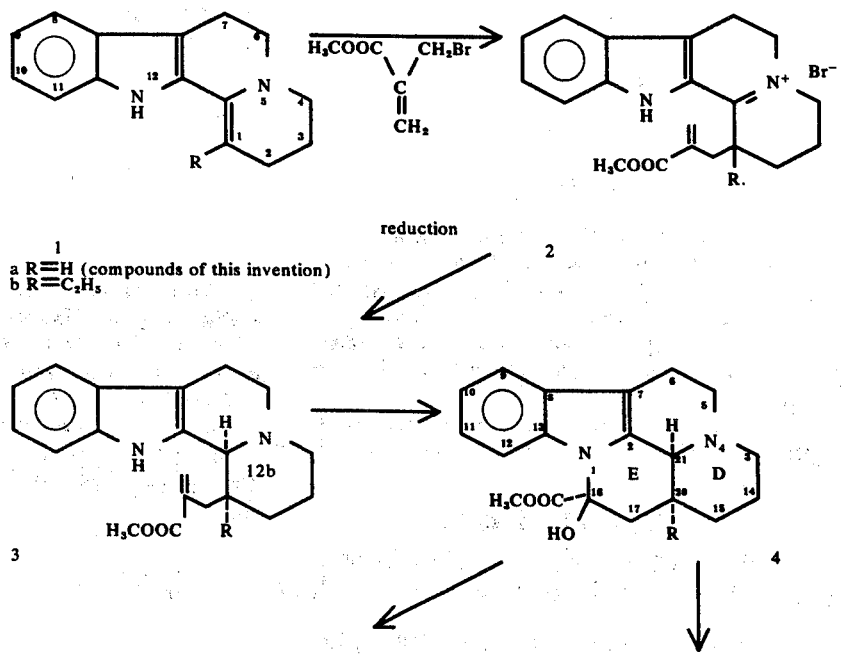

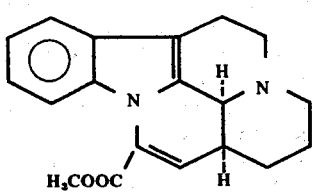
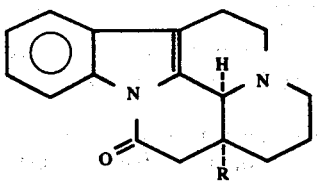

5

7

DIAGRAM I

Amide (7) may also be prepared according to the reaction scheme illustrated below in Diagram II. Enamine (10) is alkylated with ethyl bromoacetate or iodoacetate, to give immonium salt (9) which is reduced with sodium borohydride or by hydrogenation in the presence of 10% palladium-over-charcoal, and resulting derivative (8) is then treated with sodium ethoxide in absolute ethanol or with potassium t-butoxide is anhydrous benzene, to give cis-quinolizidine derivative (7) in which the D/E rings are cis-fused.

dium phosphate (3.6 g) and monosodium phosphate (1.4 g) is suspended.

Methyl α-bromomethylacrylate (2 ml) is added under a nitrogen atmosphere. The reaction mixture is stirred during 15 hours at room temperature after which the inorganic phase is filtered off. Sodium borohydride is added to the filtrate, while cooling over an ice-bath. When reduction is complete (as ascertained by thin-layer chromatography), the material is poured into water and extracted with chloroform to give 1.2 g

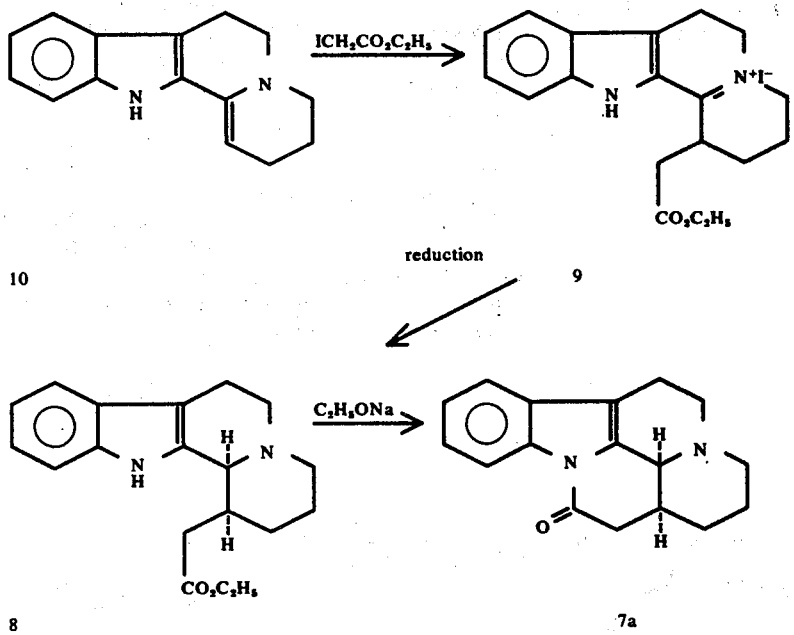

DIAGRAM II

The following examples illustrate the invention.

The melting points are determined with a Leitz microscope or with a Kofler block and are corrected; the NMR spectra are measured with a Perkin-Elmer type $R_{12}$ apparatus using tetramethylsilane as zero reference; the mass spectra are recorded with an AEI type MS9 apparatus.

For purposes of clarity, the alkaloid nomenclature is frequently used (J. Le Men and W. I. Taylor, Experientia, 1965, 21, 508).

EXAMPLE 1 (DIAGRAM I)

a. 1,2,3,4,6,7,12,12b-Octahydro-1-(β-methoxycarbonylallyl)-indolo[2,3a]-quinolizine (Compound 3a, R = H)

1 g of enamine (compound 1, R = H) is dissolved in methanol (40 ml) in which a buffer mixture of disoof a brown lacquer which is chromatographed through a silica column. The fractions eluted with benzene-ether (99:1) contain methyl α-bromoethylacrylate together with polyalkylated compounds.

Derivative (3a) (0.560g) is separated as a colorless lacquer with benzene-ether 95:5.

I.R. Spectrum (CH Cl$_3$): 3460–3370 cm$^{-1}$ (>N—h), 2860–2810–2755 cm$^{-1}$ (Bohlmann's bands), 1715 cm$^{-1}$

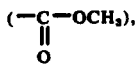

1630 cm$^{-1}$ (>C=CH$_2$)

U.V. Spectrum (EtOH): in neutral medium and in alkaline medium: = 227 nm (log $\epsilon$ = 4.40), 276 nm (log $\epsilon$ = 3.79), 285 nm (log $\epsilon$ = 3.81), 292 nm (log $\epsilon$ = 3.74), 360 nm (log $\epsilon$ = 2,84), in acidic medium: = 222 nm (log $\epsilon$ = 4.37), 274 nm (log $\epsilon$ = 3.82), 281 nm (log $\epsilon$ = 3.79), 291 nm (log $\epsilon$ = 3.68), 360 nm (log $\epsilon$ = 3.08).

Mass Spectrum: peaks at m/e 324 (M$^+$), 323, 309, 293, 265, 263, 249, 247, 225, 224, 197, 184, 170, 169, 144, 143, 96.

NMR Spectrum:
1 proton ($N_a$—H at 8.8 ppm
4 aromatic H's between 6.9 and 7.5 ppm
2 ethylenic H's: 2 doublets centered at 6.1 and 5.5 ppm (J = 2 Hz)
3 H (methyl ester); singlet at 3.70 ppm
1 H ($C_{12b}$) at 3.40 ppm.

The presence of Bohlmann's bands (2900–2700 cm$^{-1}$) in I.R. and the position of the signal, in nuclear magnetic resonance, of hydrogen ($C_{12b}$) at 3.40 ppm make it possible to contemplate a trans-quinolizidine linking of the C/D rings.

b. (±) 20-Deethyl-vincamine (Compound 4a, R = H)

Osmium tetraoxide (70 mg) is added to a solution of compound 3a (410 mg) in dioxan (145 ml) and water (45 ml).

After one hour of contact, with stirring, the medium turns black. Periodic acid (1.9 g) is added thereto.

The reaction mixture is stirred for a further 24 hours in the absence of light, after which potassium iodide and a normal sodium arsenite solution are added thereto until the material is decolorized and a pH of 7.5 is obtained. The reaction mixture is then extracted with chloroform to give 338 mg of a brown lacquer. Crystallization from acetone gives 150 mg of (±)-20-deethyl-vincamine (4a). M.p. (inst.) = 248° C (corr.).

Analysis: for $C_{19}H_{22}O_3N_2$ Calc. % : C, 69.92; H, 6.79; N, 8.58; Found : C, 70.21; H, 7.09; N, 8.10.

Mass Spectrum : peaks at m/e 326 (M$^+$), 325, 311, 308, 267, 265, 264, 248, 238, 224, 209, 196, 180, 168, 167, 144.

I.R. Spectrum: (CH Cl$_3$): bands at 1740 cm$^{-1}$ (ester) and 3520 cm$^{-1}$ (OH)

U.V. Spectrum: maximum absorption at 229 nm (log $\epsilon$ = 4.44), 276, (3.88), 282 (3.89), 292 (3.74) in ethanol solution, and maximum absorption at 270 (3.93), 316 (3.53) in hydrochloric medium (11N).

N.M.R. Spectrum: After two minutes, there are noted:
4 aromatic protons between 7.6 and 7 ppm
1 3-proton singlet at 3.80 ppm representing the methyl ester. The position of this signal is characteristic of the configuration contemplated at the level of carbon $C_{16}$.
1 broad signal at 5.1 ppm, characteristic of the proton at $C_{21}$ (this signal appears at 4.3 ppm in CDCl$_3$). after 4 hours of contact, due to a dehydration, appears the signal of the ethylenic proton carried by carbon 17 (doublet centered at 6.5 ppm J = 7 Hz). Corresponding product 5 was isolated.

Said spectra confirm the structure of compound 4a which possesses the stereochemistry of vincamine (compound 4b, R = $C_2H_5$) and, consequently, may be named ($\mp$)-deethyl-vincamine.

This compound is characterized by a cis-quinolizidine (C/D) linking and a cis-fusion of the D/E rings.

Isomer 6a, having the formula:

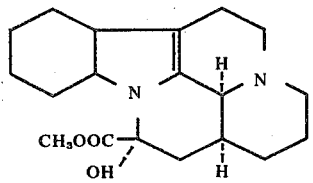

which is differentiated by the reverse stereochemistry at the level of carbon 16, could be isolated in the course of the purifications.

c. 20-Deethyl-apovincamine (compound 5)

This compound is obtained from 20-deethyl-vincamine (compound 4a) by dehydration in acidic medium.

IR Spectrum (CDCl$_3$): band at 1730 cm$^{-1}$ (ester); absence of OH band at 3520 cm$^{-1}$.

EXAMPLE 2 (±) -20-Deethyl-eburnamonine (Compound 7a, R = H) Diagram I.

To a mixture of compound 4a (20 mg) in tetrahydrofuran (10 ml) is added lithium-aluminum hydride (15 mg). After refluxing during 3 hours, the reaction mixture is evaporated, taken up into 2N HCl (5 ml) and is then heated during 3 hours over a boiling water-bath. The chloroform extract of the alkalinized reaction mixture gives, after evaporation, 17 mg of a brown lacquer which is chromatographed using a thick layer of silica, to give 3 mg of (±)-20-deethyl-eburnamonine, identified by its IR spectrum and by thin layer chromatography in various eluent mixtures (see Example 4b).

EXAMPLE 3

($\div$)-Vincamine (Compound 4b, R = $C_2H_5$). Diagram I.

The procedure of Example 1 is used, using enamine 1b (R = $C_2H_5$) as starting material. Enamine 1b (360 mg) is dissolved in ethanol-acetonitrile (1:1). After adding methyl α-bromomethyl acrylate (0.7 ml), the reaction medium is refluxed with stirring, under a nitrogen atmosphere, during 20 hours. The reaction mixture is then made alkaline and sodium borohydride is added to the cooled reaction mixture (ice-bath) until complete reduction of the immonium salt (2b, R = $C_2H_5$) (ascertained by thin layer chromatography). The material is poured into water and extracted with chloroform. On evaporation, the chloroform phases leave a brown lacquer which is osmylated in the presence of periodic acid, in the same manner as compound 3a. Extraction with chloroform gives a black lacquer (120 mg). ($\div$)-Vincamine 4b (25 mg) is separated by crystallization from acetone.

M.p. = 190°–232° C (fusion - solidification - fusion).

The compound was compared with the naturally occurring material (E. SCHLITTLER, Helv. Chim. Acta, 1953, 36, 2017;M. PLAT and coll.; Bull. Soc. Chim. de Fr., 1962, 5, 1082).

The I.R., U.V., mass and N.M.R. spectra and the melting point are identical.

EXAMPLE 4 (DIAGRAM II)

a. 12H, 12bH-1,2,3,4,6,7-hexahydro-1-ethoxycarbonylmethylindolo[2,3-a]quinolizine (Compound 8, intermediate)

Enamine 1a (R = H) (1 g) dissolved in ethyl iodoacetate (3 cc) is stirred under a nitrogen atmosphere, at 110° C, during 4 hours. After cooling, excess reagent is removed by washing with hexane.

The residue containing immonium iodide (9) may be reduced in two different ways:

a. It is dissolved in ethanol (5ml) and is then reduced with sodium borohydride (120 mg), added portionwise. The reaction mixture is poured into salt water and is extracted with chloroform, to give 1.13 g of crude product.

b. It is taken up into ethanol and is then hydrogenated at ordinary pressure and temperature over 10% palladium-over-charcoal during 3 hours. After filtration and evaporation of the filtrate, the same crude material is obtained as under (a).

The material is purified through a column of alumina with 30 times the weight of adsorbent and eluted with benezene-chloroform (1:1), to give 460 mg (Yield 33%) of derivative (8). M.p. = 160° C (benzene/hexane, 1/1)

Analysis: for $C_{19}H_{24}O_2N_2$: Calculated, %: C, 73.04; H, 7.74; O, 10.24; N, 8.97; Found %: C, 72.84; H, 7.69 O, 10.19; N, 8.85.

U.V. Spectrum (neutral ethanol): 276 (3.564), 284 (3.581), 292 (3.494).

IR Spectrum (Nujol): 3365 (NH), 1710 (ester) (CHCl$_3$): 3465 (NH), 2860-2805-2655 (Bohlmann's bands), 1725 (ester).

N.M.R. Spectrum: broad signal 8.1 N—H ($\delta$, CDCl$_3$) q 4 —O—CH$_2$—CH$_3$ broad signal 3.4 H at 21 t 1.1 CH$_3$—CH$_2$—O Mass Spectrum: peaks at m/e 312 (M$^+$, 100 %), 311, 283, 267, 239, 224, 197, 184, 170.

b. 1,2,3,5,6,12,13,13a-octahydro-12-oxo[3,2,1-d,e]-indolo-[3,2,1i,j]-pyrido-[1,5]-naphthyridine or 20-deethyl-eburnamonine (Compound 7a)

A solution of the trans-cis derivative 8 (460 mg) in 0.1M sodium ethoxide (30 ml) is stirred at 50° C during 3 hours. The reaction mixture is then poured into salt water and is extracted with chloroform, to give 400 mg of (±) cis-cis derivative (7). (cis-quinolizidine fusion and cis-fusion of rings D/E). M.p. = 156° C (hexane)

Analysis: $C_{17}H_{18}ON_2$ Calculated %: C, 76.66; H, 6.81; N, 10.52; Found %: C, 76.39; H, 6.83; N, 10.33.

U.V. Spectrum (neutral ethanol): 242.5 (4.238), 267 (3.957), 295 and 303 (3.602).

I.R. Spectrum (CHCl$_3$ or Nujol) band at 1705 cm$^{-1}$ (lactam); no Bohlmann's bands.

N.M.R. Spectrum: m 8.4 H at 10 m 4.3 H at 21

Mass Spectrum: peaks at m/e 266 (m$^+$, 100%), 265, 237.

Both enantiomers of (±)-20-deethyl-eburnamonine could be isolated after crystallization of the tartrates ( (+)paratoluyltartaric acid) from methanol to constant optical rotations; there were obtained two bases having the following optical rotations:

$[\alpha]_D^{20}$ CHCl$_3$ = +104° and −104°

The process described in the present application makes it possible to obtain (±)vincamine whose useful therapeutic properties are well known, and also new vincamine derivatives. Said new derivatives were also found to possess a vasodilatator action, particularly at the cerebral level, and are therapeutically useful to control deficiencies of the cerebral circulation.

The following comparative tests between deethylvincamine and vinciamine have been carried out.

1. Acute toxicity in mice

The dosage of test material which, on intravenous administration in mice causes the death of 50% of the test animals is determined (death rate is determined after 10 days of observation).

TABLE 1

|  | Deethylvincamine | Vincamine |
|---|---|---|
| LD$_{50}$ i.v. (mg/kg) | 40 | 62 |

2. Survival time of mice under a confined atmosphere

Mice are individually placed in sealed 250 ml glass jars. Survival time is measured taking respiratory failure as a criterion of death.

The test materials are administered as aqueous solutions:

either intraperitoneally, in which case the animals are submitted to the test 30 minutes after injection, or orally, in which case the animals are submitted to the test 1.5 hour after administration.

The dosage of material (ED$_{50}$) which protects 50% of the test animals is determined: is considered as protected, a mouse having a survival time greater by a factor of at least 30% with respect to the average survival time of the reference animals.

The resulting data are tabulated in following Table 2.

TABLE 2

| | Deethylvincamine | | Vincamine | |
|---|---|---|---|---|
| Route | Dosage (mg/kg) | Number of mice protected | Dosage (mg/kg) | Number of mice protected |
| i.p. | 3 | 1/6 | 1 | 0/6 |
| | 9 | 3/6 | 5 | 1/6 |
| | 27 | 6/6 | 25 | 4/6 |
| | ED$_{50}$ | 8.0 | ED$_{50}$ | 18 |
| p.o. | 7.5 | 0/6 | 25 | 2/6 |
| | 15 | 1/6 | 50 | 4/6 |
| | 30 | 4/6 | 100 | 5/6 |
| | ED$_{50}$ | 24.5 | ED$_{50}$ | 40 |

3. Electroencephalographic consequences of cerebral hypoxia induced by temporary ischemia in rat In spinal rat, the effects of a temporary cerebral ischemic hypoxia obtained by ligation of the vertebral arteries and clamping, during 60 seconds, of the carotid arteries, are investigated at the level of the electrocorticogram (recorded in fronto-parietal lead). The following times are determined:

on the one hand, the "cortical resistance" time, i.e., the period of time which elapses between failure of the cerebral circulation and the appearance, in the recording, of the "dectric silence"disappearance of cortical electrogenesis), and on the other hand, the "cortical recovery" time, i.e., the period of time which elapses between unclamping of the carotid arteries and the reappearance of a cortical electrogenesis.

The test materials are administered intravenously 5 minutes prior to ischemia. The results obtained in the treated animals are compared with those obtained in a lot of reference animals according to Student's "t" method.

The results obtained are tabulated in following Table 3.

TABLE 3

| Treatment | Dosage mg/kg i.v. (a) | Cortical resistance time (seconds) (b) | Cortical recovery time (seconds) (b) |
|---|---|---|---|
| Normal saline | (11) | 22.3 ± 0.6 | 19.8 ± 1.3 |

TABLE 3-continued

| Treatment | Dosage mg/kg i.v. (a) | Cortical resistance time (seconds) (b) | Cortical recovery time (seconds) (b) |
|---|---|---|---|
| solution | | | |
| Vincamine | 2.5 (6) | 22.2 ± 1.2 | 21.8 ± 2.0 |
| | 5 (7) | 23.4 ± 0.9 | 19.9 ± 3.0 |
| Deethylvincamine | 0.25(6) | 25.3 ± 1.2 | 20.3 ± 2.7 |
| | 0.5 (6) | 24.3 ± 1.6 | 14.3 ± 1.1 (*) |

(a) The figures in parentheses correspond to the number of animals used.
(b) Mean values ± standard deviations from mean.
(*) Significant difference (P < 0.05) with respect to the controls.

4. Electroencephalographic consequences of a cerebral hypoxia induced by temporary asphyxia in rat The effects of an asphyxic cerebral hypoxia, obtained by a two-minute interruption of the artificial respiration of a curarized rat are investigated at the level of the electro-corticogram (recorded in fronto-parietal lead) by determining:

on the one hand the "cortical resistance" time, i.e., the period of time which elapses between the discontinuation of artificial respiration and the appearance in the recording of the "electric silence" (disappearance of cortical electrogenesis), on the other hand, the "cortical recovery" time, i.e., the period of time which elapses between the resumption of artificial respiration and the reappearance of a cortical electrogenesis.

The test materials are administered intravenously 5 minutes prior to asphyxia. The results obtained in the treated animals are compared with those obtained in a lot of reference animals, according to Student's "t" method.

The results obtained are tabulated in following Table 4.

TABLE 4

| Treatment | Dosage mg/kg i.v. (a) | Cortical resistance time (seconds) (b) | Cortical recovery time (seconds) (b) |
|---|---|---|---|
| Normal saline solution | (16) | 77.8 ± 2.9 | 42.3 ± 7.3 |
| Vincamine | 2.5 (6) | 83.3 ± 6.4 | 55.5 ± 20.2 |
| | 5.0 (6) | 89.0 ± 7.6 | 32.8 ± 1.8 |
| Deethylvincamine | 0.5 (6) | 84.2 ± 4.5 | 38.8 ± 5.9 |
| | 1 (7) | 78.0 ± 5.6 | 23.0 ± 5.0 (*) |

(a) The figures in parentheses correspond to the number of animals used.
(b) Mean values ± standard deviations from mean
(*) Significant difference (P<0.05) with reference to the controls.

5. Electroencephalographic consequences of cerebral hypoxia induced by temporary asphyxia in cat The effects of an asphyxic cerebral hypoxia, obtained by temporary discontinuance of the artificial respiration of a curarized cat are investigated at the level of the electrocorticogram (recorded in parieto-occipital lead), by determining:

on the one hand, the "cortical resistance" time, i.e., the period of time which elapses between the discontinuance of the artificial respiration and the appearance in the recording of the "electric silence" (disappearance of cortical electrogenesis), on the other hand, the "cortical recovery" time, i.e., the period of time which elapse between the resumption of artificial respiration and the reappearance of a cortical electrogenesis. The resumption of artificial respiration is effected in all cases 45 seconds after appearance of the cortical silence.

The test materials are administered intravenously 5 minutes prior to asphyxia. The results obtained in the treated animals are compared with those obtained in a lot of reference animals, according to Student's "t" method.

The results obtained are tabulated in Table 5.

TABLE 5

| Treatment | Dosage mg/kg i.v.(a) | Cortical resistance time (seconds) (b) | Cortical recovery time (seconds) (b) |
|---|---|---|---|
| Normal saline solution | (12) | 108 ± 5.6 | 27.3 ± 2.3 |
| Vincamine | 2.5 (8) | 101 ± 13.9 | 24.6 ± 3.4 |
| | 5 (8) | 101 ± 5.6 | 19.6 ± 1.4 (*) |
| Deethylvincamine | 0.5 (6) | 98 ± 10.8 | 19.0 ± 2.0 (*) |

(a) The figures in parentheses correspond to the number of animals used.
(b) Mean values ± standard deviations from mean
(*) Significant difference (P <0.05) with respect to the controls.

To conclude while deethylvincamine possesses an acute toxicity substantially of the same order of magnitude as that of vincamine in mice, by the i.p. and p.o. routes, with respect to cerebral hypoxia induced by placing the animals under a confined atmosphere, deethylvincamine exhibits a marked protective activity (increase of the survival time with respect to the controls) markedly superior to that of vincamine.

In rat, by the intravenous route, with respect to a temporary cerebral hypoxia of ischemic or asphyxic origin, deethylvincamine displays a marked protective activity (decrease, with respect to the controls, of the time required for the resumption of cortical electrogenesis after discontinuance of the ischemia or asphyxia) at dosages of 0.5 mg/kg and 1 mg/kg i.v., respectively; under the same experimental conditions, vincamine is free from any protective activity at dosages of 2.5 and 5 mg/kg, i.v.

Finally, in cat, by the intravenous route, with respect to temporary cerebral hypoxia of asphyxic origin, deethylvincamine exhibits a protective activity (decrease, with respect to the controls, of the time required for the resumption of cortical electrogenesis after discontinuance of the asphyxia) at the dosage of 0.5 mg/kg, i.v.; under the same experimental conditions, the protective activity of vincamine is apparent only at a tenfold dosage of 5 mg/kg i.v.

It is clear that deethylvincamine possesses in an unexpected manner properties markedly superior to those of vincamine, the activity/toxicity ratio being much more favourable in the case of deethylvincamine.

Having now described our invention what we claim as new and desire to secure by letters patent is:

1. 20 -Deethyl-vincamine, under its racemic and optically active forms, having the formula:

and its stereoisomer, having the formula:

* * * * *